(12) United States Patent
Schick

(10) Patent No.: US 7,052,603 B2
(45) Date of Patent: May 30, 2006

(54) SINGLE-USE MANIFOLD FOR AUTOMATED, ASEPTIC TRANSFER OF SOULUTIONS IN BIOPROCESSING APPLICATIONS

(75) Inventor: Karl G. Schick, Madison, WI (US)

(73) Assignee: Scilog, Inc., Middleton, WI (US)

( * ) Notice: Subject to any disclaimer, the term of this patent is extended or adjusted under 35 U.S.C. 154(b) by 236 days.

(21) Appl. No.: 10/764,624

(22) Filed: Jan. 26, 2004

(65) Prior Publication Data

US 2004/0155066 A1    Aug. 12, 2004

Related U.S. Application Data

(62) Division of application No. 10/172,082, filed on Jun. 14, 2002, now Pat. No. 6,712,963.

(51) Int. Cl.
*B01D 15/08* (2006.01)

(52) U.S. Cl. ............... 210/198.2; 210/137; 210/195.2; 210/257.2; 210/321.75; 210/321.84; 210/416.1; 210/656; 222/63

(58) Field of Classification Search ............... 210/137, 210/198.2, 257.2, 258, 321.65, 321.75, 195.2, 210/416.1, 321.84, 656, 659; 222/63
See application file for complete search history.

(56) References Cited

U.S. PATENT DOCUMENTS

| | | | |
|---|---|---|---|
| 4,433,973 A | 2/1984 | Kurtz et al. | |
| 4,484,599 A * | 11/1984 | Hanover et al. | 137/636.1 |
| 4,626,346 A | 12/1986 | Hall | |
| 4,680,109 A | 7/1987 | Yamada et al. | |
| 4,713,051 A | 12/1987 | Steppe et al. | |
| 4,818,384 A | 4/1989 | Mayer | |
| 5,076,931 A | 12/1991 | Muller | |
| 5,107,908 A | 4/1992 | Newhouse et al. | |
| 5,112,489 A | 5/1992 | Hartmann | |
| 5,200,090 A | 4/1993 | Ford et al. | |
| 5,207,642 A | 5/1993 | Orkin et al. | |
| 5,256,294 A | 10/1993 | van Reis | |
| 5,273,517 A * | 12/1993 | Barone et al. | 494/37 |
| 5,282,787 A | 2/1994 | Wortrich | |
| 5,282,972 A | 2/1994 | Hanna et al. | |
| 5,328,584 A | 7/1994 | Erickson et al. | |
| 5,340,290 A | 8/1994 | Clemens | |
| 5,350,290 A * | 9/1994 | Honings | 425/311 |
| 5,431,811 A | 7/1995 | Tusini et al. | |
| 5,480,063 A | 1/1996 | Keyes et al. | |
| 5,480,393 A | 1/1996 | Bommarito | |

(Continued)

FOREIGN PATENT DOCUMENTS

EP    1 236 644 A1    9/2002

(Continued)

OTHER PUBLICATIONS

Technical Bulletin: "MidGee Cross Flow Filters," A/G Technology Corp., 1996.

(Continued)

*Primary Examiner*—Ernest G. Therkorn
(74) *Attorney, Agent, or Firm*—Cook, Alex, McFarron, Manzo, Cummings & Mehler, Ltd.

(57) ABSTRACT

Presteralized manifolds are provided which are designed for sterile packaging and single-use approaches. Disposable tubing and flexible-wall containers are assembled via aseptic connectors. These manifolds interact with at least one remotely controlled pinch valve which engages only the outside surface of the manifold tubing. Such manifold and pinch valve systems can be used in conjunction with a peristaltic type of pump, which, together with the remotely operated pinch valve, can be operated by a controller which provides automated and accurate delivery of biotechnology fluid in an aseptic environment while avoiding or reducing cleaning and quality assurance procedures.

35 Claims, 3 Drawing Sheets

U.S. PATENT DOCUMENTS

| | | | |
|---|---|---|---|
| 5,520,816 A | 5/1996 | Kuepper | |
| 5,538,405 A | 7/1996 | Patno et al. | |
| 5,589,076 A | 12/1996 | Womack | |
| 5,597,486 A | 1/1997 | Lutz | |
| 5,680,960 A | 10/1997 | Keves et al. | |
| 5,693,229 A | 12/1997 | Hartmann | |
| 5,776,345 A | 7/1998 | Truitt et al. | |
| 5,791,880 A | 8/1998 | Wilson | |
| 5,947,689 A | 9/1999 | Schick | |
| 5,958,244 A | 9/1999 | Hartmann | |
| 6,240,952 B1* | 6/2001 | Schroeder | 137/240 |
| 6,299,769 B1 | 10/2001 | Falkvall et al. | |
| 6,350,382 B1 | 2/2002 | Schick | |
| 6,375,847 B1 | 4/2002 | Hartmann | |
| 6,569,687 B1* | 5/2003 | Doktycz et al. | 436/180 |
| 2002/0043487 A1 | 4/2002 | Schick | |
| 2004/0001906 A1* | 1/2004 | Carhuff et al. | 426/130 |
| 2005/0109795 A1* | 5/2005 | Furey et al. | 222/63 |

FOREIGN PATENT DOCUMENTS

| | | |
|---|---|---|
| FR | 2 567 406 A1 | 1/1986 |
| FR | 2 785 830 | 5/2000 |
| WO | WO 99/02245 | 1/1999 |
| WO | WO 03/106266 | 12/2003 |

OTHER PUBLICATIONS

Operating Instructions: "MiniKros Sampler System," Microgon Inc., 1995.

Technical Bulletin: "The MiniKros Sampler System," Spectrum Microgon, May 1996.

Technical Bulletin: "Microgon Techniques for Processing Uniform Latex Particles," Microgon Inc., 1992.

William F. Blatt, Lita Nelsen, Eliseo M. Zipiliyan, and Mark C. Porter, "Rapied Salt Exchange by Coupled Ultratiltration and Dialysis in Anisotropic Hollow Fibers," Separation Science, 7(3) pp. 271-284, 1972.

William F. Bowers and Rudy H. Haschmeyer, "A Versatile Small-Volume Ultrafiltration Cell- Analytical Biochemistry, " 25, pp. 549-556, 1968.

UltraTec Filtration System, "Operations Manual Version: 1.28," SciLog, Inc., Apr., 1997.

Patent Abstract of Japan, Japan Organo Co Ltd, Publication Date Mar. 14, 1995, Publication No. 07068257.

Patent Abstract of Japan, Asahi Cehm Ind Co Ltd, Publication Date Mar. 24, 1998, Publication No. 10076143.

Si-Hassen, et al., "Optimisation of an intermittent cross-flow filtration process of mineral suspensions," Journal of Membrane Science, 118 (1996) 185-198.

Carere, "Study of hydrodynamic parameters in the cross-flow filtration of guar gum pseudoplastic solutions," Journal of Membrane Science, 174 (2000) 135-145.

Webpage of HyClone at www.hyclone.com, undated.

Webpage of "Integrate Solution for Biopharmeaceutical Fluid Handling" at www.tc-tech.com, undated.

Filvek, "Volumetric Disposable Liquid Filling System Schematic," Innovative Technology Practical Solutions, Brochure.

International Search Report for International Application No. PCT/US 03/18980, with International filing date of Jun. 13, 2003.

* cited by examiner

SINGLE-USE MANIFOLD FOR AUTOMATED, ASEPTIC TRANSFER OF SOULUTIONS IN BIOPROCESSING APPLICATIONS

RELATED APPLICATIONS

This application is a division of application No. 10/172,082, filed Jun. 14, 2002, now U.S. Pat. No. 6,712,963.

FIELD OF THE INVENTION

The invention generally relates to the aseptic transfer of solutions out of one or more biological fluid and/or process fluid storage or supply containers. Single-use manifold systems carry out transfers needed in bioprocessing applications. With the invention, automated dispensing is accomplished, preferably in association with one or more remotely controlled pinch valves.

BACKGROUND OF THE INVENTION

Good manufacturing practices and governmental regulations are at the core of any pharmaceutical, biotechnology and bio-medical manufacturing process or procedure. Such manufacturing processes and procedures as well as associated equipment must undergo mandated, often lengthy and costly validation procedures.

For example, the equipment used for the separation and purification of biomedical products must, for obvious reasons, meet stringent cleanliness requirements. The cleaning validation of new or re-commissioned purification equipment (such as equipment for preparative chromatography or tangential flow filtration) may require as many as 50 test-swabs of exposed surfaces and subsequent biological assays of such test-swabs. For a single piece of purification equipment, the associated and reoccurring cost of a single cleaning validation may readily exceed multiple thousands of dollars.

To reduce such cleaning validation costs and expenses, and/or to reduce the occasions when cleaning is needed or required, the pharmaceutical and biotech industries are increasingly employing, pre-sterilized, single-use, plastic tubing and collapsible, plastic bags for solution transfer and storage. Sterilization is accomplished by exposing the complete tube/bag manifold to gamma irradiation, or to an ethylene oxide atmosphere. The pre-sterilized, aseptically packaged tube/bag manifolds are commercially available (currently from TC Tech; HyClone; St Gobain Performance Plastics, for example) and are used for the manual transfer of solutions. Typically, the solution transfer procedure requires a technician to operate a peristaltic pump and to manually open and close tube clamps for diverting the solution from the reservoir to the storage bags. Although this procedure reduces the cleaning efforts and cleaning validation expense, operator interaction and time still are required, and these approaches are dependent upon operator expertise for consistent accuracy and precision.

Dispensing approaches having automated features (which can include sensors, monitors and programmable controllers) are generally known. Keys et al. U.S. Pat. No. 5,480,063 and U.S. Pat. No. 5,680,960 describe fluid dispensing units which control fluid volumes in conjunction with a closed loop approach, which these patents suggest can avoid the need for venting. The fluid to be dispensed exits the closed loop apparatus through a fill tube, as directed by a controller. Such approaches do not address the cleaning needs and/or cleaning validation costs and expenses, were these types of systems to be used in pharmaceutical and biotech industries for dispensing, directing, combining or separating biological or chemical fluids.

Prior systems can incorporate diaphragm valves, which come into direct contact with the process solution, and these valves are a potential source of contamination. Thus diaphragm valves require costly cleaning validation procedures.

It has been found that, by proceeding in accordance with the present invention, significant cost savings and better performance can be realized in a system which incorporates automated, aseptic manifolds within the field of technology which embraces pre-sterilized, single-use plastic tubing and containers having at least one collapsible portion. The components which contact the biological or chemical fluid are each presterilized and disposable after use.

SUMMARY OF THE INVENTION

The present invention is directed to manifold units which are presterilized and disposable, making them single-use units which are sterilized and packaged so as to be usable "off the shelf" and which thus directly address the problem of tedious and time consuming cleaning and testing at the use site. Multiple embodiments are disclosed. Each includes tubing lengths and a plurality of single-use storage or collection bags, each having multiple inlet and/or outlet passages which are selectively openable and closeable. The tubing lengths interact with one or more pinch valves which are operable remotely. Remote operation is automated by a controller programmed to carry out procedures according to a selected embodiment.

It is a general object of the present invention to provide improved single-use manifolds for automated, aseptic transfer of solutions in bio-processing or chemical processing applications.

Anther object of the present invention is to provide improved apparatus and method which combine pinch valve use with disposable, sterilized manifold dispenser units.

Another object of this invention is to provide improved apparatus and method which greatly reduce the expenditure of time and resources devoted to cleaning procedures for transfer equipment used in pharmaceutical and biological industries and laboratories where contamination of biological and/or chemical fluids cannot be tolerated.

An aspect of the present invention is to reduce the need for validation procedures for equipment used in separation and purification of fluids such as in conjunction with the preparation, separation and dispensing of bio-medical products.

Another aspect of this invention is that it handles cleanliness requirements for procedures such as fluid dispensing, preparative chromatography and tangential flow filtration while automating operation thereof.

These and other objects, aspects, features, improvements and advantages of the present invention will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
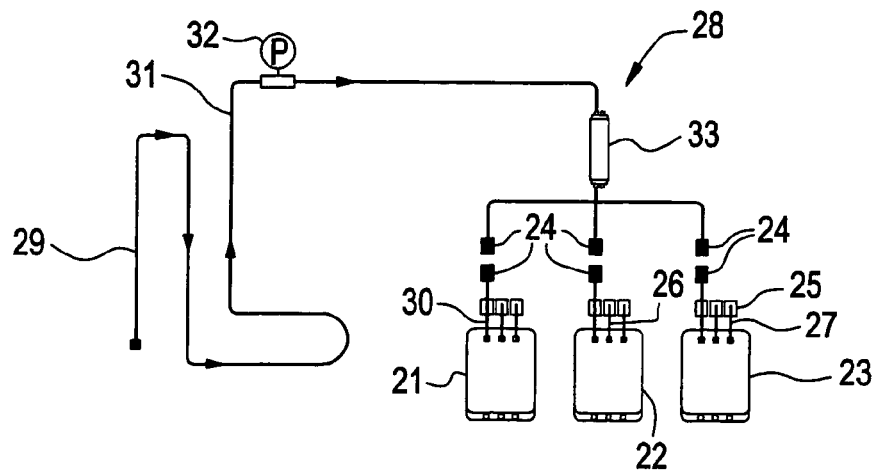
FIG. 1 is a somewhat schematic illustration of a single-use, presterilized system which is especially suitable for solution transfer and collection.
Figure 2:
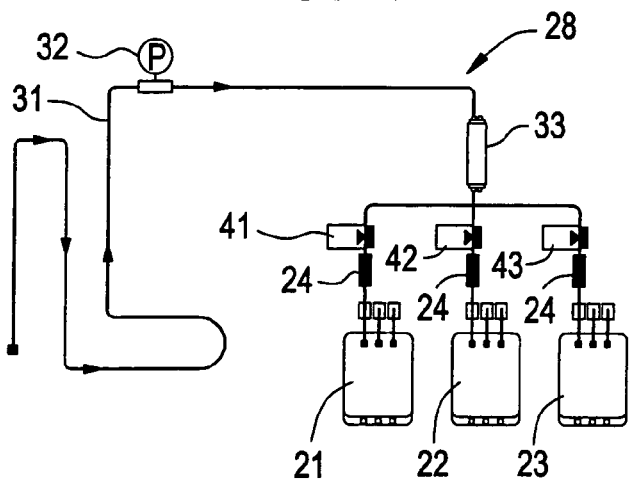
FIG. 2 is an illustration of the single-use system of FIG. 1 in operative association with pinch values, at least one of which is remotely operable.
Figure 3:
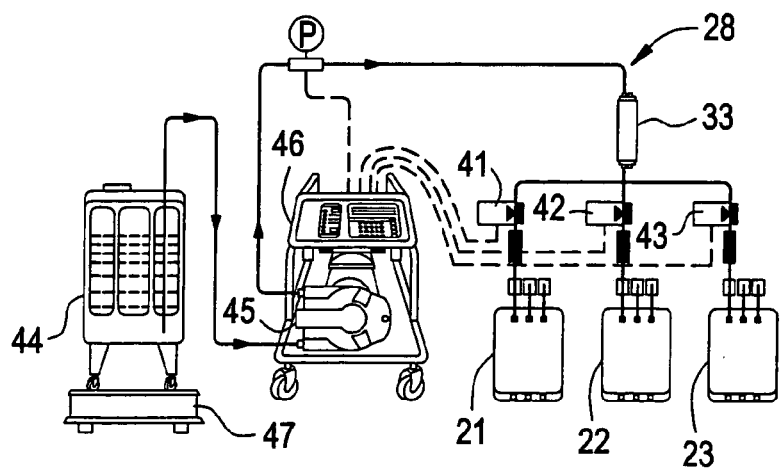
FIG. 3 is an illustration of the combination of the features of FIG. 1 and FIG. 2, shown with means for use to transfer solution through the system.

A system particularly designed for use as an automated, aseptic solution transfer system is illustrated in FIGS. 1–3. Fluids processed according to this invention are variously referred to herein as biotechnology fluids, pharmaceutical fluids, chemical fluids, and so forth. These are understood to be solutions, liquids, gas-including systems, and the like. In general, these are referred to herein as biotechnology fluid or fluids.

In the pharmaceutical and biotechnology industries, media preparation departments typically prepare the solutions used in a solution production protocal which follows good manufacturing practices. Media preparation departments are responsible for maintaining solution recipes, preparing and storing buffer solutions and other tasks demanding consistency and accuracy. For example buffer solutions are prepared in large vats, then pumped through a sterilizing filter, such as one having a porosity of 0.1μ. Typically such solutions need to be filled into presterilized, single use storage bags for later use. A media preparation department may also be responsible for providing inoculating solutions to the operators of a bioreactor. At the completion of a bioreactor batch, the reactor broth often is filled into sterile storage bags for later processing.

FIG. 1 shows single-use, presterilized components of the invention. Generally, these disposable components are a manifold and transfer tubing assembly and a plurality of bags. A plurality of single-use storage/collection bags 21, 22, 23 are shown. Each has three tube connections. The primary inlet tubing consists of an aseptic connector 24 and a manual shut-off clamp 25, each of generally known construction. During solution storage, the aseptic connector is covered with an end cap (not shown) to protect the connector 24 from contamination. The manual shut-off clamp 25 is closed during solution storage. These are shown on a first tube connection 30.

The second tube connection 26 consists of a short piece of tubing connected to the bag with a closed manual shut-off clamp. This tubing and clamp arrangement is used to relieve any gas and/or pressure build-up inside the bag during the filling operation. The third tube connection 27 is identical to the second connection and includes a short piece of tubing and a clamp. This can be used as an auxiliary inlet and/or outlet for recirculation of the bag contents.

During a typical bag-filling operation, the first and/or last collection bag can serve the purpose of quality control bags. Often these quality control bags will be smaller in volume, such as one liter. During the initial system priming cycle, the first such quality assurance (QA) bag is filled with process solution. At the end of the dispensing cycle when all of the bags containing the product of the operation, usually larger in volume that the QA bag(s), have been filled, the second QA bag is filled. The solutions contained in the QA bags are subsequently analyzed for contamination or for other quality assurance needs.

When the bag-filling process is completed, the manual shut-off clamps on each bag are closed and the aseptic tube connections are disconnected. During storage, the aseptic connector ends are protected with end caps (not shown)

Turning now to the single-use, sterilized manifold and transfer tubing assembly of FIG. 1, one such unit is generally shown at 28. This represents a generalized manifold for automated solution transfer. An inlet end portion 29 of transfer tubing 31 of the unit 28 is for communication with a container, such as a vat, of solution, typically sterile solution. Sterilized manifold and transfer tubing assembly 28 is shown with an optional, in-line pressure sensor 32 and a single-use sterilizing filter 33. An end portion having serially connected end portions are downstream of the illustrated filter 33. By a suitable movement imparting device, solution moves from the vat or reservoir through the sensor 32 (if included) and filter 33 and then is serially diverted into the single-use, sterilized storage bags.

FIG. 2 shows a plurality of pinch valves 41, 42, 43 and their respective relative positions with respect to the storage bags. Some or all of the valves can be operated remotely and typically will be pneumatically or electrically activated. A typical set up will have capacity for up to twelve pneumatically actuated pinch valves or more. A like number of storage bags can be accommodated. FIG. 2 shows the relative positions of the pinch valves in association with the optional pressure sensor and the single-use, sterilizing filter. FIG. 3 shows the relative position of the manifold and transfer tubing assembly 28 with the vat 44 and the pump head of a pump unit 45. Preferably, the pump is a high-accuracy, low-shear peristaltic pump which provides gentle and reproducible bag filling. An example is a Watson Marlow 620 RE peristaltic pump head.

Access to the storage bags is provided via the pinch valves. The pinch valves are normally closed and, typical pneumatic pinch valves require pressurized air (for example 80–100psi) to open. When such a pinch valve is pressurized, solution is allowed to enter the storage bag while the air in the bag escapes through an integral vent filter. The pinch valve(s) are pneumatic or electrically operated pinch valves (currently available from ACRO Associates, Inc). They are installed external to the tubing and are operated by a multi valve controller (currently available from SciLog Inc.), or another computer-based process logic control (PLC) device. The external pinch valves divert the solution inside the manifold without compromising the sterile environment inside the tubing. Diaphragm valves used in other systems are in constant contact with the process solution, whereas pinch valves do not contact the process solution.

The optional, disposable pressure sensor 22 continuously monitors the filter back pressure. This sensor can provide information to a suitable controller to avoid undesired events. For example, a controller can issue an alarm when a safe, user-defined, pressure limit has been exceeded, indicating that the capacity of the sterilizing filter has been exhausted. Details in this regard are found in U.S. Pat. Nos. 5,947,689 and 6,350,382 and in U.S. patent application Publication No. 2002/0043487, each being incorporated by reference hereinto.

The controller can be a stand-alone unit or be associated with another device. In a preferred arrangement, the controller is associated with the pump unit 45. This is shown at 46 in FIG. 3. Whatever form it takes, the controller controls operation of the remotely operable pinch valve(s). The batch filling rate as well as the batch volume delivered into each storage bag is user-programmable via software residing in the controller. The controller provides automated bag filling by volume, weight or based on filling time and pump rate.

Typically, a user-determined program will be provided for the automated filling of storage bags according to FIGS. 1–3. This is described in terms of a SciPro controller of Scilog, Inc., generally described in U.S. Pat. No. 5,947,689 and No. 6,350,382 and U.S. patent Application Publication No. 2002/0043487. With these approaches, excessive pressure build-up, as well as associated leaks and bag failures are prevented. For example, when so programmed, the controller will stop all pumping action when a user-defined safe pressure limit is exceeded.

An exemplary solution transfer program for controlling the manifold is as follows. In a SciPro edit mode, the user enters and stores a multi-bag metering program. The following is an example of a simple program to fill three, 20-liter storage bags 21, 22, 23.

| | | |
|---|---|---|
| 000 | START | The following program steps are entered in an edit mode |
| 001 | CW | Motor Runs Clockwise |
| 002 | RUN | Motor is tuned "ON" |
| 003 | V 100000 | Pinch Valve 41 is Energized, other pinch valves are De-energized |
| 004 | RATE: 5.0 l/min | Pump Rate 5 liters per minute |
| 005 | TIME: 00:04:00 | Pump Runs 4 minutes, Bag 21 is filled with 20 Liters |
| 006 | STOP | Pump "Off", |
| 007 | V 020000 | Pinch Valve 42 is Energized, other valves pinch are De-energized |
| 008 | TIME: 00:00:02 | 2 Second Time delay |
| 009 | RUN | Pump "ON" |
| 010 | RATE: 5.0 l/min | Pump Rate 5 liters per minute |
| 011 | TIME: 00:04:00 | Pump Runs 4 Minutes, Bag 22 is filled with 20 Liters |
| 012 | STOP | Pump "Off" |
| 013 | V 003000 | Pinch Valve 43 is Energized, other valves are De-energized |
| 014 | TIME: 00:00:02 | 2 Second Time Delay |
| 015 | RUN | Pump "ON" |
| 016 | RATE: 5.0 l/min | Pump Rate 5.0 liters per minute |
| 017 | TIME: 00:04:00 | Pump Runs 4 Minutes, Bag 23 is filled with 20 Liters |
| 018 | STOP | Pump "Off" |
| 019 | V 000000 | All Pinch Valves are De-energized |
| 020 | COUNT: 1 | The Program Steps 000 to 020 are executed once |
| 021 | END | |

Changes in the RATE and TIME program steps will accommodate any storage bag volume. Additional "RUN" program blocks can be inserted to increase the number of bags (up to 12 in the example) to be filled. However, an analogous software program can be generated in which storage bags are filled based upon either VOLUME or WEIGHT program commands. A scale with an appropriate capacity is required for bag filling by weight. An optional scale or load cell 47 can be provided to supply data to the controller in this regard. It will be appreciated that this embodiment meters user-defined volumes of fluid, they automatically switches to the next empty storage bag to be filled.

Figure 4:
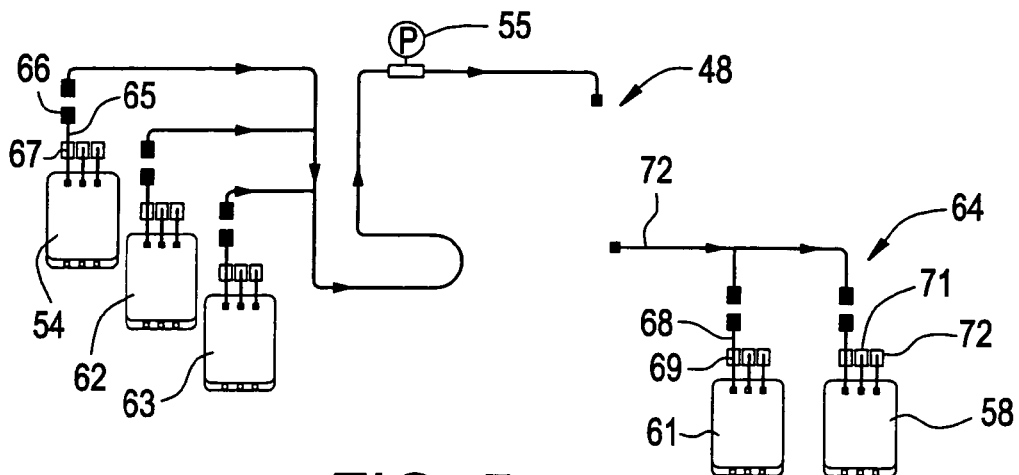
FIG. 4 is a somewhat schematic illustration of a single-use, presterilized system which is especially suitable for use in automated preparative chromatography.
Figure 5:
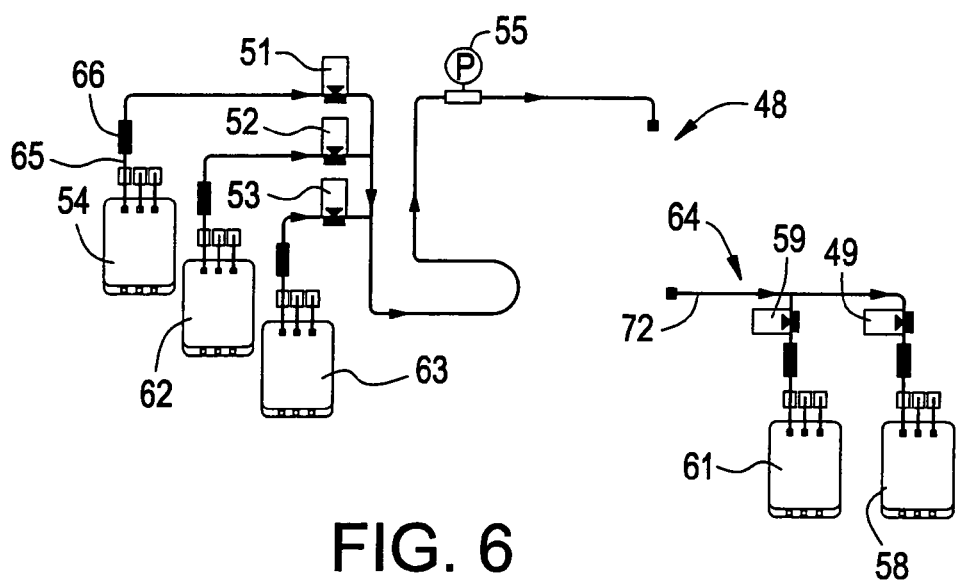
FIG. 5 is an illustration of the single-use system of FIG. 4 in operative association with pinch valves, at least one of which is remotely operable.
Figure 6:
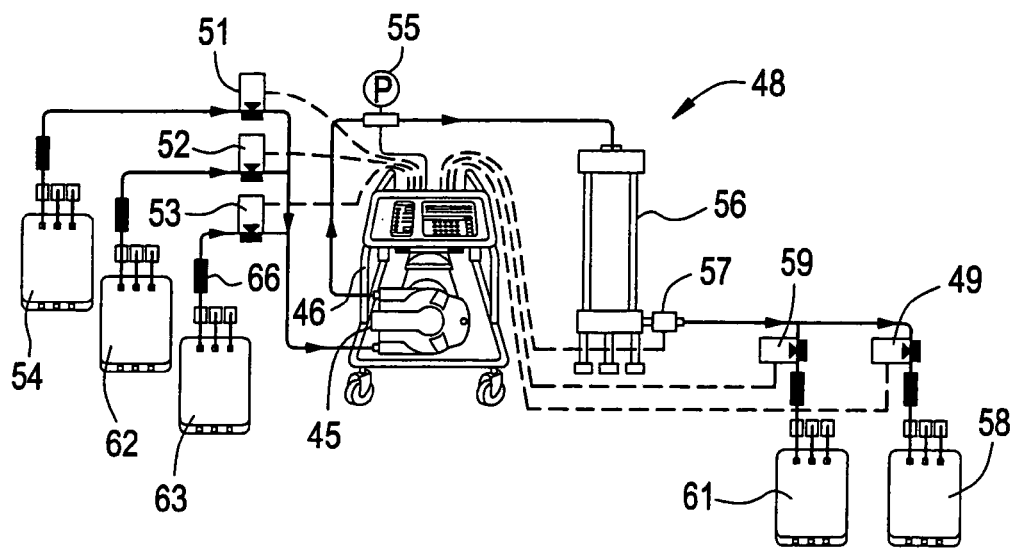
FIG. 6 is an illustration of the combination of features of FIG. 4 and FIG. 5, shown with means for use in transferring solution through the system.

A second embodiment, which is generally illustrated in FIGS. 4–6, achieves automated preparative chromatography. In preparative chromatography, process solution containing the bio-molecule of interest is pumped through a column of gel-like particles (stationary phase) suspended in a liquid. The bio-molecule of interest specifically interacts (via ion-ion interactions, hydrophobic interactions, size exclusion, affinity, for example) with the stationary phase thereby retarding the progress of the bio-molecule through the column. Ideally, other dissolved biomaterials will interact only weakly with the stationary phase and thus will exit the column quickly.

The result is a concentration as well as a separation of the bio-molecule from the rest of the process solution matrix. The introduction of an elution buffer will change the local chemical environment of the stationary phase, thereby causing the bio-molecule to be released and thus able to be collected outside the column in a relatively small volume of elution buffer.

In automated preparative chromatography, the column containing the stationary phase first is washed and/or equilibrated with an appropriate buffer solution. This wash and/or equilibration cycle is followed by a loading cycle during which the process solution is pumped through the column. The bio-molecule of interest adheres to the stationary phase. The loading cycle can take many hours, depending on the process solution volume and pump rate with which the solution is pumped through the column. The loading cycle is followed by a second wash cycle to remove any un-adsorbed biomaterial off the column.

An elution buffer then is introduced to remove the bio-molecule from the column. This removal of the bio-molecule is accomplished either with a step gradient or a linear gradient. After peak collection has been completed, the chromatography column is regenerated and re-equilibrated using appropriate buffer solutions as generally known in the art.

Manifold and transfer tubing assembly 48 represents a generalized manifold for automating preparative chromatography procedures. In operation, and utilizing the controller system, the exemplary pneumatically controlled pinch valve 51 is pressurized and thus opened, thereby providing access to the wash and/or equilibration buffer bag 54. At a user-definable pump rate, the wash buffer is pumped through a disposable, in-line pressure sensor 55, through a bubble trap (not shown), through the chromatography column 56, and through a detector or UV flow cell 57. On exiting the flow cell, the wash/equilibration buffer is collected in a waste container or bag 58 while pinch valve 49 is pressurized and thus open.

During the loading cycle, pinch valves 51 and 49 are opened/pressurized, while the pinch valves 52, 53 and 59 remain closed. The pump unit 45 pumps the process solution through the manifold system 48, the column 56 and the flow cell 57 and is collected in the waste container or bag 57. In some chromatography applications, the process solution exiting the flow cell needs to be stored separately in a "process receiving bag" (not shown) for possible re-processing. Another pinch valve (not shown) would provide access to such a "process receiving bag".

The loading cycle is followed by a wash cycle (valves 51 and 49 are open/pressurized, all other pinch valves are closed) which carries away any un-absorbed material from the column to waste. By opening pinch valves 53 and 49, elution buffer in bag 63 is introduced into the column and is initially pumped to waste. However, when the signal from the UV detector 57 exceeds a user-defined value, pinch valve 59 is opened thereby providing access to a peak collection bag 61 while valve 49 is closed. On the backside of the eluted peak, valve 59 is again closed, while at the same time, valve 49 is opened.

After the material of interest has been collected in bag 61, the chromatographic column 56 requires regeneration and re-equilibration. The column regeneration process is readily automated via access to appropriate buffer solutions (not shown), which are generally as known in the art. Depending on the underlying chromatographic complexity of the application, access to five or six buffer solutions may be required, and these can be provided in their own single-use bags as desired. Similarly, if multiple product peaks are to be collected, additional peak collection bag(s) as well as additional pinch valve(s) may have to be incorporated into manifold and transfer tubing assembly 48.

The single-use, presterilized components of the manifold and transfer tubing assembly 48, shown as a feed section, and of a second tube and bag assembly 64 for chromatographed fluid are shown in FIG. 4. Each of the single storage/collection bags 54, 62, 63 shown in FIG. 4 has three tube connections. The primary inlet tubing 65 consists of an aseptic connector 66 and a manual shut-off clamp 67. During solution storage, the aseptic connector is covered with an end cap to protect the connector from contamination. The manual shut-off clamp is closed during solution storage.

The second tube and bag assembly 64 consists of a short piece of tubing 68 connected to the bag with a closed manual shut-off clamp 68. The second tubing/clamp arrangement 71 is used to relieve any gas and/or pressure build-up inside the bag during the filling operation. The third tube connection 72 is identical to the second tubing/clamp arrangement 71 and is used as an auxiliary inlet/outlet for recirculation of the bag contents.

The single-use storage/collection bags 58 and 61 are connected to the remaining tube manifold 72 as shown in FIG. 4 and FIG. 5. FIG. 5 shows the relative positions of the pinch valves 51, 52, 53, 49 and 59 and the position of the pressure sensor 55. FIG. 6 shows the insertion of the manifold tubing into the peristaltic pump head 45 as well as connections to the chromatography column 56 and the detector 57.

In a typical chromatography application, the single-use storage bags 54 (for wash buffer), 52 (for process solution) and 63 (for elution buffer) have been previously filled, for example by using the embodiment of FIG. 1–3. When the chromatography run is completed, the manual shut-off clamps on each collection bag 58 (for waste), 61 (for peak collection), and for process receiving (when desired, not shown) are closed, and the aseptic tube connections are disconnected. During storage, the aseptic connector ends are protected with end caps.

Referring further to the SciPro controller programmed for controlling the manifold arrangement for chromatography, a mode thereof allows entry and storage of a sequence of simple commands, i.e. RUN, RATE, TIME, VOLUME, P LIMIT 1 and Valve States such as V=000000 (all pinch valves are closed) or V=123456 (all pinch valves are open).

This controller mode is organized in subprogram blocks. The terminating statement of a program block can be a "VOLUME", "TIME", "P LIMIT D1 (or D2)" or "N LIMIT D1 (or D2)" statement. The statement "P LIMIT D1=5%" reads: "Positive Slope Signal of Detector D1 with a Threshold Value of 5% Full Scale (FS)". See the Chromatography Program Example.

| 000 | START | Start of $1^{st}$ Wash Cycle |
| 001 | CW | Clockwise Motor Direction |
| 002 | RUN | Starts Motor |
| 003 | RATE 0.25 L/M | Pump Rate During Wash Cycle |
| 004 | V 100050 | Wash Buffer 51 Diverted to "Waste" 49 |
| 005 | VOLUME 1.0 Liters | 4 Minutes, End of $1^{st}$ Wash Cycle, TV = 1.0 L |
| 006 | RATE 1.00 L/M | Loading Rate, Start of Loading Cycle |
| 007 | V 020050 | Process Solution (52) Diverted to "Waste" (49) |
| 008 | TIME: 00:02:00 | 2 Minutes, End of Loading Cycle, TV = 3.0 L |
| 009 | RATE 0.25 L/M | Start of $2^{nd}$ Wash Cycle |
| 010 | V 100050 | Wash Buffer (51) Diverted to "Waste" (49) |
| 011 | VOLUME 1.0 Liter | 4 Minutes, End of $2^{nd}$ Wash Cycle TV = 4.0 L |
| 012 | V 003050 | Elution Buffer (53) Diverted to "Waste" (49) |
| 013 | P LIMIT D1 = 5% | Threshold Value Detected Start of Peak Volume Collection |
| 014 | V 003400 | Elution Buffer (53) Diverted to "Collect" (59) |
| 015 | N LIMIT D1 = 10% | D1 Threshold Value, End of Peak Volume Collection |
| 016 | V 003050 | Elution Buffer (53) Diverted to "Waste" (49) |
| 017 | VOLUME 1.0 Liter | Elution Volume, End of Elution, TV = 5.0 L |
| 018 | RATE 0.50 L/M | Start of $3^{rd}$ Wash Cycle |
| 019 | V 00050 | Wash Buffer (51) Diverted to "Waste" (49) |
| 020 | TIME 00:02:00 | 2 Minutes, End of $3^{rd}$ Wash Cycle, TV = 6.0 L |
| 021 | STOP | Pump Stops, |
| 022 | V 000000 | All V-valves Closed |
| 023 | END | End of Program |

For example, in line 014, the SciPro switches from "Waste" to "Collect" when the D1 signal has a positive slope and a value greater than 5% FS (line 013). The statement "N LIMIT D1=10%" reads: "Negative Slope Signal of Detector D1 with a Threshold Value of 10% FS". In line 016, the controller switches from "Collect" to "Waste" when the D1 signal has a negative slope (back side of peak) and a value of 10% FS (line 15).

The user can edit and/or modify the values of: RUN, RATE, TIME, VOLUME, P LIMIT 1, N LIMIT D1 and Valve States at any time during a chromatography run. User-designed application programs can be uploaded or downloaded from an external computer at any time by utilizing the computer's hyper terminal.

It will be appreciated that, with this embodiment, sequential scheduling of events are achieved. These include sequential scheduling of wash, load and elution cycles. The controller can initiate buffer selection, loading and peak volume collection. Typical in-line concentration detectors can be Wedgewood UV and/or pH detectors, which have outputs of 4–20MA outputs which can be monitored simultaneously. A typical pump is a Watson Marlow 620 R peristaltic pump head capable of generating 60psi at a pump rate of 15 liters per minute.

User-defined detection threshold levels are used for valve switching and peak volume collection. All solution-handling parameters, such as pump rates, column pressure, and valve positions can be monitored and documented in real time and can be printed out or electronically archived.

In a third embodiment, automated tangential flow filtration is carried out using a modified system designed for this use. Previously referenced U.S. Pat. No. 5,947,689 and U.S. Pat. No. 6,350,382 and U.S. Published Patent Application No. 2002/0043487 disclose the automation of tangential flow filtration (TFF) procedures. These are combined with the use of disposable, single-use manifolds, which also include disposable pressure sensors and single-use, collapsible storage bags and the use of remotely operated pinch valve(s).

Figure 7:
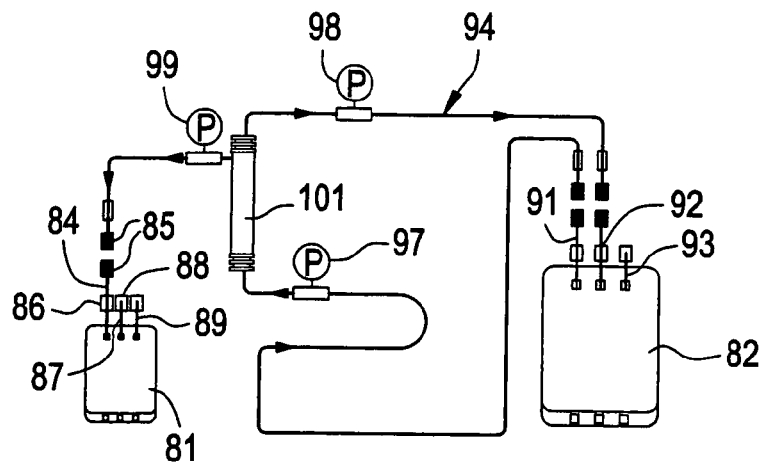
FIG. 7 is a somewhat schematic illustration of a single-use, presterilized system which is especially suitable for automated tangential flow filtration procedures.
Figure 8:
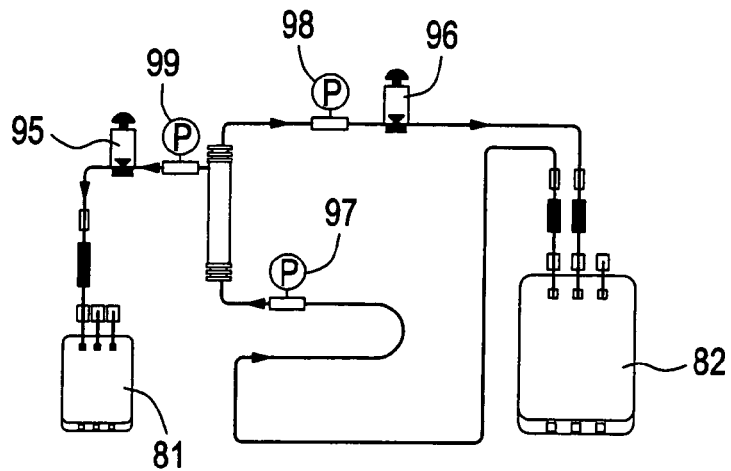
FIG. 8 is an illustration of the single-use system of FIG. 7 in operational association with pinch valves, at least one of which is remotely operable.
Figure 9:
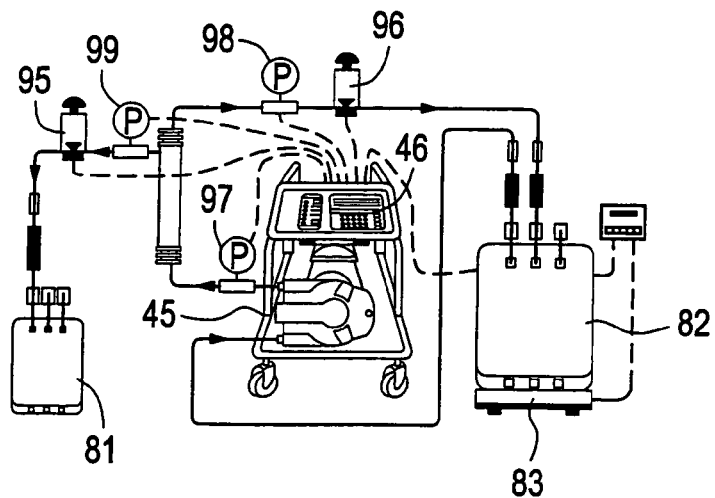
FIG. 9 is an illustration of the combination of the features of FIG. 7 and FIG. 8, shown with means for use to transfer solution through the system.

A typical TFF application that utilizes a single-use, pre-sterilized manifold is shown in FIGS. 7–9. FIG. 7 shows the disposable, pre-sterilized components, including a tubing filtered fluid section having a permeate collection bag 81 as well as a process solution bag 82 within a filtration flow-through section of the tubing. These are aseptically sealed and in a pre-sterilized (for example, irradiated) package. At the beginning of the TFF application, the permeate collection bag 81 is empty and deflated and has been aseptically connected to the TFF manifold. The process solution bag was previously filled, such as by using the system of FIGS. 1–3. The process solution bag 82 is placed onto an optional scale 83 and connected aseptically to the rest of the system. In some applications, weight information can be conveyed to the controller in carrying out the control logic.

The pre-sterilized components of this embodiment are shown in FIG. 7. The permeate collection bag 81 has three tube connections. The primary inlet tubing 84 consists of an aseptic connector 85 and a manual shut-off clamp 86. During solution storage, the aseptic connector is covered with an end cap to protect the connector from contamination. The manual shut-off clamp is closed during solution storage.

The second tube connection consists of a short piece of tubing 87 connected to the bag with a closed manual shut-off clamp 88. The second tubing and clamp arrangement is used to relieve any gas and/or pressure build-up inside the bag during the filling operation. The third tube connection 89 can be identical to the second tubing and clamp arrangement and is used as an auxiliary inlet and outlet for recirculation of bag contents.

Similarly, the process solution bag 82 has three inlet and/or outlet tube connections. The first tube connection 91 is used as an outlet to pump solution out of the bag. The second tube connection 92 serves as a return inlet to accommodate the re-circulated retentate. The third tube connection 93 again serves to relieve any excessive gas and/or pressure build-up inside the bag.

The permeate collection bag and the process solution bag are connected to the filtration tube manifold, generally designated at 94 in FIG. 7. FIG. 8 shows the relative positions of the pinch valves 95 and 96 and the position of three pressure sensors 97, 98, 99. FIG. 9 shows the insertion of the manifold tubing into the head of the peristaltic pump unit 45.

Prior to starting the pump unit 45, all of the manual shut-off clamps are opened except those clamps that relieve any gas and/or pressure build-up inside the bags. Initially the valve 95 is closed and the valve 96 is open, while the pump unit 45 starts to recirculate the solution contained in the process solution bag 82 through a tangential flow filter system 101. The air volume contained in the tubing and tangential flow filter system 101 ends up in the process solution bag 82 where it is vented to the outside through a sterilizing air filter (not shown). Once the optimal pump recirculation rate has stabilized, pinch valve 95 is opened and permeate is collected.

The micro filtration or ultra filtration can be carried out either by constant rate or by constant pressure. Software programs which are suitable to automate the filtration process through the use of the controller 46 are described in U.S. Pat. No. 5,947,689 and U.S. Pat. No. 6,350,382 and U.S. Patent Application Publication No. 2002/00434487.

It will be understood that the embodiments of the present invention which have been described are illustrative of some of the applications of the principles of the present invention. Numerous modifications may be made by those skilled in the art without departing from the true spirit and scope of the invention.

The invention claimed is:

1. A manifold system for biotechnology uses, comprising:
    a manifold unit which is pre-sterilized and disposable so as to be adapted for single-time usage, including:
        (a) at least one length of tubing having at least one inlet end portion, at least one outlet end portion, an outside surface, and an inside surface which is sterilized for passage of a biotechnology fluid therethrough,
        (b) at least one single-use bag having a primary access port, and
        (c) an aseptic connector means for operatively connecting said length of tubing with said primary access port of the single-use bag; and
    a plurality of pinch valves, at least one of which is remotely operable in response to a signal remote from said pinch valve, each said pinch valve engages said outside surface of the length of tubing at a discrete location therealong, each said pinch valve independently selectively allowing or stopping flow of the biotechnology fluid through said inside surface of the length of tubing at said discrete location for that pinch valve.

2. The manifold system in accordance with claim 1, wherein said primary access port of the single-use bag includes a shut-off clamp.

3. The manifold system in accordance with claim 1, wherein said single-use bag further includes access port means for releasing gas or pressure build-up from said bag.

4. The manifold system in accordance with claim 1, wherein said single-use bag further includes an auxiliary access port.

5. The manifold system in accordance with claim 1, wherein said single-use bag further includes access port means for releasing gas or pressure build-up from said bag and further includes an auxiliary access port.

6. The manifold system in accordance with claim 5, further including a shut-off clamp for said access port means and for said auxiliary access port.

7. The manifold system in accordance with claim 1, further including a singleuse sterilizing filter positioned along said length of tubing such that the biotechnology fluid flows therethrough at a location upstream of said outlet and portion.

8. The manifold system in accordance with claim 1, wherein said system is for automated aseptic fluid transfer, wherein said outlet end portion of the tubing has a plurality of serially arranged outlet passageways having one of said aseptic connector means for operable connection with said single-use bag, and wherein each said pinch valve controls passage of the biotechnology fluid from the tubing to the single-use bag.

9. The manifold system in accordance with claim 8, further including a single-use sterilizing filter positioned along said length of tubing such that the biotechnology fluid flows therethrough at a location upstream of said outlet end portion.

10. The manifold system in accordance with claim 8, further including a disposable pressure sensor positioned along said length of tubing such that the biotechnology fluid flows therethrough at a location upstream of said outlet end portion.

11. The manifold system in accordance with claim 9, further including a disposable pressure sensor positioned along said length of tubing such that the biotechnology fluid flows therethrough at a location downstream of said sterilizing filter and upstream of said outlet end portion.

12. A manifold system for biotechnology uses, wherein said system is for automated, aseptic fluid transfer, comprising:
   a manifold unit which is pre-sterilized and disposable so as to be adapted for single-time usage, including:
      (a) at least one length of tubing having at least one inlet end portion, at least one outlet end portion, an outside surface, and an inside surface which is sterilized for passage of a biotechnology fluid therethrough,
      (b) a plurality of single-use bags, each having a primary access port,
      (c) aseptic connector means for operatively connecting said length of tubing with said primary access port of at least one of said single-use bags, and
      (d) said outlet end portion of the tubing has a plurality of serially arranged outlet passageways having one of said aseptic connector means for operable connection with said single-use bag; and
   a plurality of pinch valves, at least one of which is remotely operable in response to a signal remote from said pinch valve, each said pinch valve engages said outside surface of the length of tubing at a discrete location therealong, each said pinch valve independently selectively allowing or stopping flow of the biotechnology fluid through said inside surface of the length of tubing at said discrete location for that pinch valve, and wherein each said pinch valve controls passage of the biotechnology fluid from the tubing to each said single-use bag.

13. The manifold system in accordance with claim 12, further including a singleuse sterilizing filter positioned along said tubing such that the biotechnology fluid flows therethrough at a location upstream of said outlet passageways.

14. The manifold system in accordance with claim 13, further including a disposable pressure sensor positioned along said tubing such that the biotechnology fluid flows therethrough at a location downstream of said sterilizing filter and upstream of said outlet passageways.

15. The manifold system in accordance with claim 12, further including a disposable pressure sensor positioned along said tubing such that the biotechnology fluid flows therethrough at a location upstream of said outlet passageways.

16. The manifold system in accordance with claim 12, wherein said primary access port of the single-use bag includes a shut-off clamp.

17. The manifold system in accordance with claim 12, wherein said singleuse bag further includes access port means for releasing gas or pressure build-up from said bag.

18. The manifold system in accordance with claim 12, wherein said singleuse bag further includes an auxiliary access port.

19. The manifold system in accordance with claim 12, wherein said singleuse bag further includes access port means for releasing gas or pressure build-up from said bag and further includes an auxiliary access port.

20. The manifold system in accordance with claim 19, further including a shut-off clamp for said access port means and for said auxiliary access port.

21. A manifold and pump system for biotechnology uses, comprising:
   a manifold unit which is pre-sterilized and disposable so as to be adapted for single-time usage, including:
      (a) at least one length of tubing having at least one inlet end portion, at least one outlet end portion, an outside surface, and an inside surface which is sterilized for passage of a biotechnology fluid therethrough,
      (b) at least one single-use bag having an access port, and
      (c) an aseptic connector means for operatively connecting said length of tubing with said access port of the single-use bag;
   a plurality of pinch valves, at least one of which is remotely operable in response to a signal remote from said pinch valve, each said pinch valve engages said outside surface of the length of tubing at a discrete location therealong, each said pinch valve independently selectively allowing or stopping flow of the biotechnology fluid through said inside surface of the length of tubing at said discrete location for that pinch valve; and
   a pump unit which engages said outside surface of the length of tubing at a selected location upstream of said discrete location for the pinch valve.

22. The manifold and pump system in accordance with claim 21, further including a controller which controls operation of said pump unit and of said pinch valve.

23. The manifold and pump system in accordance with claim 22, wherein said controller is a programmable unit.

24. The manifold and pump system in accordance with claim 22, wherein said controller is programmable and is included in said pump unit.

25. The manifold and pump system in accordance with claim 21, wherein said pinch valve is pneumatically operated.

26. The manifold and pump system in accordance with claim 21, wherein said pinch valve is electronically operated.

27. A manifold and pump system for biotechnology uses, wherein said system is for automated, aseptic fluid transfer, comprising:
   a manifold unit which is pre-sterilized and disposable so as to be adapted for single-time usage, including:
      (a) at least one length of tubing having at least one inlet end portion, at least one outlet end portion, an outside surface, and an inside surface which is sterilized for passage of a biotechnology fluid therethrough,
      (b) a plurality of single-use bags, each having an access port,
      (c) aseptic connector means for operatively connecting said length of tubing with said access port of at least one of said single-use bags, and
      (d) said outlet end portion of the tubing has a plurality of serially arranged outlet passageways having one of said aseptic connector means for operable connection with said single-use bag;

a plurality of pinch valves, at least one of which is remotely operable in response to a signal remote from said pinch valve, each said pinch valve engages said outside surface of the length of tubing at a discrete location therealong, each said pinch valve independently selectively allowing or stopping flow of the biotechnology fluid through said inside surface of the length of tubing at said discrete location for that pinch valve, and wherein each said pinch valve controls passage of the biotechnology fluid from the tubing to each said single-use bag; and a pump unit which engages said outside surface of the length of tubing at a selected location upstream of said discrete location for the pinch valve.

28. An automated manifold and pump system for biotechnology uses, comprising:

a manifold unit which is pre-sterilized and disposable so as to be adapted for single-time usage, including:
(a) at least one length of tubing having at least one inlet end portion, at least one outlet end portion, an outside surface, and an inside surface which is sterilized for passage of a biotechnology fluid therethrough,
(b) at least one single-use bag having an access port, and
(c) an aseptic connector means for operatively connecting said length of tubing with said single-use bag;

a plurality of pinch valves, at least one of which is remotely operable, and each said pinch valve engages said outside surface of the length of tubing;

a pump unit which engages said outside surface of the length of tubing at a selected location upstream of said pinch valve; and a controller which controls operation of said pump unit and of said pinch valve, said controller having control logic which dictates the timing of opening and closing of said remotely operable pinch valve.

29. The automated system in accordance with claim 28, wherein said control logic of the controller determines the extent of filling of the single-use bag by processing data monitored by the system to achieve filling of the single-use bag by volume, by weight, or by pump rate and filling time.

30. The automated system in accordance with claim 28, wherein said control logic of the controller dictates the rate of pumping of said pump unit.

31. An automated manifold and pump system for biotechnology uses, wherein said system is for automated, aseptic fluid transfer, comprising:

a manifold unit which is pre-sterilized and disposable so as to be adapted for single time usage, including:
(a) at least one length of tubing having at least one inlet end portion, at least one outlet end portion, an outside surface, and an inside surface which is sterilized for passage of a biotechnology fluid therethrough,
(b) a plurality of single-use bags, each having an access port,
(c) an aseptic connector for operatively connecting said length of tubing with said access port of at least one of said single-use bags, and
(d) said outlet end portion of the tubing has a plurality of serially arranged outlet passageways having one of said aseptic connectors for operable connection with said single-use bag;

a plurality of pinch valves, at least one of which is remotely operable, and each said pinch valve engages said outside surface of the length of tubing at a discrete location therealong and controls passage of the biotechnology fluid from the tubing to each said single-use bag;

a pump unit which engages said outside surface of the length of tubing at a selected location upstream of said discrete location for the pinch valve; and a controller which controls operation of said pump unit and of said pinch valve, said controller having control logic which dictates the timing of opening and closing of said remotely operable pinch valve.

32. The automated system in accordance with claim 31, wherein said control logic of the controller dictates the rate of pumping of said pump unit.

33. The automated system in accordance with claim 31, wherein said control logic of the controller determines the extent of filling of the single-use bag by processing data monitored by the system to achieve filling of the single-use bag by volume, by weight, or by pump rate and filling time.

34. The automated system in accordance with claim 31, wherein said control logic activates pumping action of said pump unit and opens a first remotely operable pinch valve for a length of time needed to pump a selected volume or weight of biotechnology fluid into a first said single-use bag associated with said first remotely operable pinch valve, wherein said control logic activates pumping action of said pump unit and opens a second remotely operable pinch valve for a length of time needed to pump a selected volume or weight of biotechnology fluid into a second said single-use bag associated with said second remotely operable pinch valve, and wherein said control logic activates pumping action of said pump unit and opens a further remotely operable pinch valve for a length of time needed to pump a selected volume or weight of biotechnology fluid into a further said single-use bag associated with said second remotely operable pinch valve until a user-selected number of singleuse bags are filled.

35. The automated system in accordance with claim 31, wherein said control logic activates pumping action of said pump unit and opens a first remotely operable pinch valve for a length of time needed to pump a selected volume or weight of biotechnology fluid into a first said single-use bag associated with said first remotely operable pinch valve, and wherein said control logic activates pumping action of said pump unit and opens a further remotely operable pinch valve for a length of time needed to pump a selected volume or weight of biotechnology fluid into a further said single-use bag associated with said second remotely operable pinch valve until a user-selected number of single-use bags are filled.

* * * * *

UNITED STATES PATENT AND TRADEMARK OFFICE
CERTIFICATE OF CORRECTION

| | | |
|---|---|---|
| PATENT NO. | : 7,052,603 B2 | Page 1 of 1 |
| APPLICATION NO. | : 10/764624 | |
| DATED | : May 30, 2006 | |
| INVENTOR(S) | : Karl G. Schick | |

It is certified that error appears in the above-identified patent and that said Letters Patent is hereby corrected as shown below:

-In the specification, column 2, line 38, please replace the word "Anther" with --Another--

-In the specification, column 3, line 2, please replace the word "values" with --valves--

-In the specification, column 6, line 5, please replace the word "switches" with --switch--

-In the specification, column 11, line 48, please replace the word "singleuse" with --single-use--

-In the specification, column 11, line 66, please replace the word "singleuse" with --single-use--

-In the specification, column 12, line 2, please replace the word "singleuse" with --single-use--

-In the specification, column 12, line 5, please replace the word "singleuse" with --single-use--

Signed and Sealed this

Twenty-second Day of May, 2007

JON W. DUDAS
*Director of the United States Patent and Trademark Office*